(12) United States Patent  (10) Patent No.: US 10,470,693 B2
Chen et al.  (45) Date of Patent: Nov. 12, 2019

(54) OPTICAL SENSING DEVICE FOR PHYSIOLOGICAL SIGNAL

(71) Applicants: METAL INDUSTRIES RESEARCH & DEVELOPMENT CENTRE, Kaohsiung (TW); Sheng-Hao Tseng, Tainan (TW); Kang-Yu Chu, Chiayi (TW)

(72) Inventors: Ming-Hui Chen, Kaohsiung (TW); Sheng-Hao Tseng, Tainan (TW); Kang-Yu Chu, Chiayi (TW)

(73) Assignees: METAL INDUSTRIES RESEARCH & DEVELOPMENT CENTRE, Kaohsiung (TW); Sheng-Hao Tseng, Tainan (TW); Kang-Yu Chu, Chiayi (TW)

( * ) Notice: Subject to any disclaimer, the term of this patent is extended or adjusted under 35 U.S.C. 154(b) by 444 days.

(21) Appl. No.: 15/390,698

(22) Filed: Dec. 26, 2016

(65) Prior Publication Data

US 2018/0177441 A1  Jun. 28, 2018

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01); *A61B 2560/0418* (2013.01)

(58) Field of Classification Search
CPC .............. A61B 5/14552; A61B 5/6826; A61B 2560/0418
USPC ....................................................... 600/344
See application file for complete search history.

(56) References Cited

U.S. PATENT DOCUMENTS

| | | | | | |
|---|---|---|---|---|---|
| 4,619,249 | A | * | 10/1986 | Landry | A61B 5/0059 362/199 |
| RE33,234 | E | * | 6/1990 | Landry | A61B 5/0059 362/199 |
| 5,413,101 | A | * | 5/1995 | Sugiura | A61B 5/14552 356/41 |
| 6,032,071 | A | * | 2/2000 | Binder | A61B 5/0059 356/369 |
| 7,349,725 | B2 | * | 3/2008 | Tsujita | A61B 1/043 600/323 |
| 9,329,124 | B2 | * | 5/2016 | Ito | G01N 21/474 |

(Continued)

FOREIGN PATENT DOCUMENTS

CN   101686803 A    3/2010
CN   205697794 U   11/2016

(Continued)

*Primary Examiner* — Navin Natnithithadha
(74) *Attorney, Agent, or Firm* — CKC & Partners Co., LLC (57) ABSTRACT

The optical sensing device is provided for receiving and transmitting a light signal. A light working area is defined according to a measurement range of the light signal. The optical sensing device includes a body, a transformation part and a signal unit. A light emitting unit and a light receiving unit are disposed at an end of the body, and the light emitting unit and the light receiving unit face the light working area. The transformation part pivots on the body. A light processing unit is disposed on the transformation part, and the light processing unit is capable of locating in the light working area for transmitting or receiving the light signal. The signal unit is configured for transmitting and processing the light signal.

10 Claims, 6 Drawing Sheets

(56) References Cited

U.S. PATENT DOCUMENTS

| | | | |
|---|---|---|---|
| 9,402,572 B2* | 8/2016 | Hu | A61B 5/14552 |
| 2011/0224518 A1* | 9/2011 | Tindi | A61B 5/14552 |
| | | | 600/323 |
| 2011/0270048 A1 | 11/2011 | Addison et al. | |
| 2013/0046159 A1* | 2/2013 | McCombie | A61B 5/14552 |
| | | | 600/324 |
| 2014/0121468 A1* | 5/2014 | Eichenholz | A61B 1/0646 |
| | | | 600/249 |
| 2014/0194712 A1* | 7/2014 | Hu | A61B 5/14552 |
| | | | 600/340 |
| 2014/0371602 A1* | 12/2014 | Ito | A61B 5/0084 |
| | | | 600/478 |
| 2015/0177134 A1* | 6/2015 | Ito | G01N 21/474 |
| | | | 356/446 |
| 2017/0172477 A1* | 6/2017 | Adusumilli | A61B 5/14552 |

FOREIGN PATENT DOCUMENTS

| | | | |
|---|---|---|---|
| TW | I270364 B | 1/2007 | |
| TW | I434673 B | 4/2014 | |
| TW | I486147 B | 6/2015 | |
| WO | 2012112885 A1 | 8/2012 | |
| WO | WO-2018229771 A1 * | 12/2018 | ........... A61B 17/122 |

* cited by examiner

OPTICAL SENSING DEVICE FOR PHYSIOLOGICAL SIGNAL

BACKGROUND

Field of Invention

The present invention relates to an optical sensing device for sensing a physiological signal. More particularly, the present invention relates to the optical sensing device having reflection and penetration measurement.

Description of Related Art

A conventional optical measurement for blood oxygen may be classified as reflection and penetration. The penetration measurement is applied to parts such as fingers, toes and earlobes. The reflection measurement is applied to parts such as forehead and limbs. In general, the penetration measurement can monitor the status of blood. However, if the thickness of the tissue to be sensed is greater than 3-4 centimeters, and then the signal would be too weak for analyzing the blood oxygen. Therefore, the penetration measurement is not suitable for the parts such as forehead and limbs. In clinical application, if health care provider needs to measure the blood oxygen at fingers and limbs, then both the reflection and penetration detectors would be needed, which is inconvenient. Therefore, it is an issue in the art about how to solve the problem.

SUMMARY

An objective of the invention is to provide an optical sensing device having reflection and penetration measurements.

Embodiments of the present invention provide an optical sensing device for receiving and transmitting a light signal. A light working area is defined according to a measurement range of the light signal. The optical sensing device includes a body, a transformation part and a signal unit. A light emitting unit and a light receiving unit are disposed at an end of the body, and the light emitting unit and the light receiving unit face the light working area. The transformation part pivots on the body. A light processing unit is disposed on the transformation part, and the light processing unit is capable of locating in the light working area for transmitting or receiving the light signal. The signal unit is configured for transmitting and processing the light signal.

In some embodiments, the transformation part includes a connector disposed on the body; and an extending part having a first end connected to the connector and a second end. The light processing unit is disposed at the second end of the extending part, and the extending part rotates along the connector.

In some embodiments, when the light processing unit locates in the light working area, the light emitting unit emits the light signal, and the light processing unit receives a penetrating light signal corresponding to the light signal. In some embodiments, the signal unit turns off the light receiving unit.

In some embodiments, when the light processing unit does not locate in the light working area, the light emitting unit transmits the light signal, and the light receiving unit receives a reflected light signal corresponding to the light signal. In some embodiments, the signal unit turns off the light processing unit.

In some embodiments, a track is formed on the body, the track extends from a second end of the body to a first end of the body, and the connector is disposed in the track.

In some embodiments, the extending part has an opening for the body to pass through.

In some embodiments, the optical sensing device includes a first transmission line. A first end of the first transmission line is electrically connected to the signal unit. An indentation is formed at the send end of the extending part for accommodating the first transmission line.

In some embodiments, a button is formed on the body for triggering the light emitting unit to emit the light signal.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
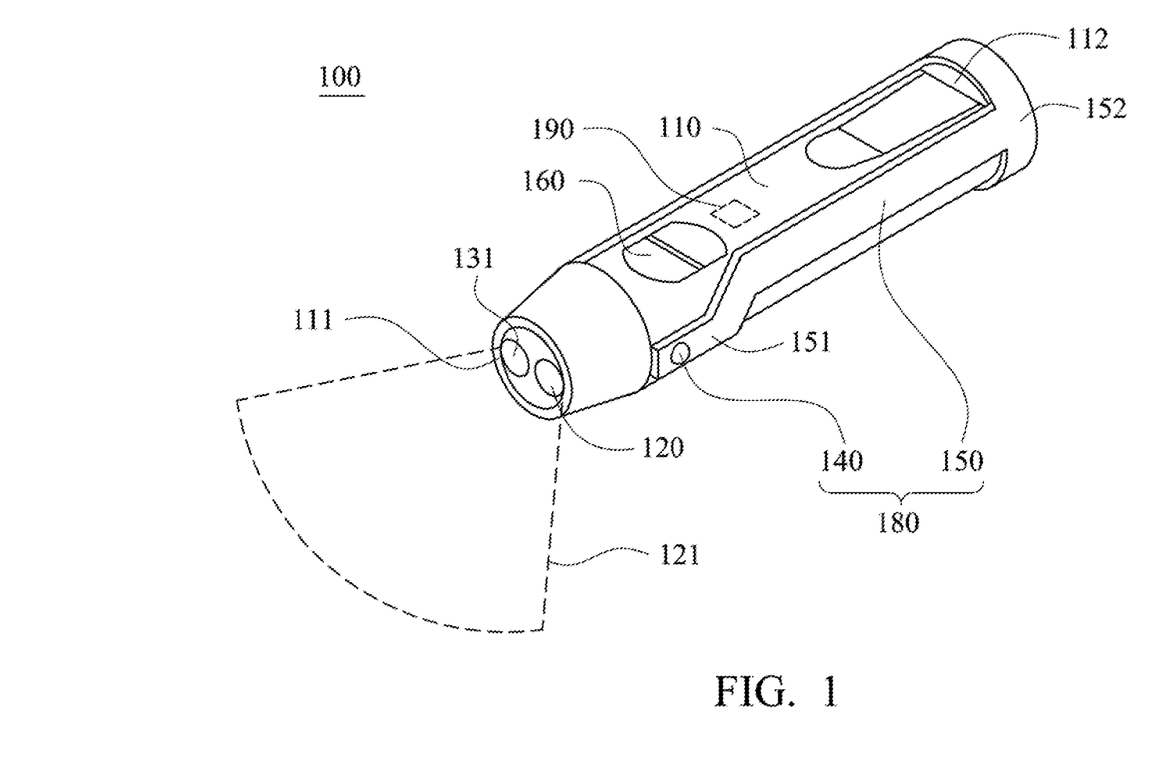
FIG. 1 is a diagram illustrating a top view of front side of the optical sensing device in the reflection mode.

The optical sensing device provided in the invention has a reflection mode and a penetration mode. The reflection mode is described first. FIG. 1 is a diagram illustrating a top view of front side of the optical sensing device in the reflection mode. Referring to FIG. 1, the optical sensing device 100 includes a body 110, a transformation part 180 and a signal unit 190 disposed in the body 110.

The body 110 has a first end 111 and a second end 112 that are opposite to each other. A light emitting unit 120 and a light receiving unit 131 are disposed at the first end 111 of the body 110 for emitting a light signal. A light working area 121 is defined based a measurement range of the light signal, but the angle and the depth of the light working area 121 are not limited in the invention. From another aspect, the light emitting unit 120 and the light receiving unit 131 face the light working area 121. The light signal emitted by the light emitting unit 120 is configured to irradiate a thick biological tissue such as forehead and limbs. The biological tissue would reflect the light signal to generate a reflected light signal which is received by the light receiving unit 131. The light receiving unit 131 is, for example, an optical sensor for transforming the reflected light signal into an electrical signal. The light receiving unit 131 transmit the electrical signal to the signal unit 190 which would transmit and process the electrical signal. The signal unit 190 may be a processor, a microprocessor, a signal processing chip or other suitable circuits. Accordingly, the reflection measurement is done.

In some embodiments, a button 160 is further disposed on the body 110 for triggering the light emitting unit 120 to emit the light signal. In some embodiments, if the button 160 is pressed for a while, the light emitting unit 120 may continuously emit the light signal. However, the mechanism to trigger the light emitting unit 120 to emit light signal is not limited in the invention. In other embodiments, the button 160 may have other functions, and the invention is not limited thereto.

Figure 2:
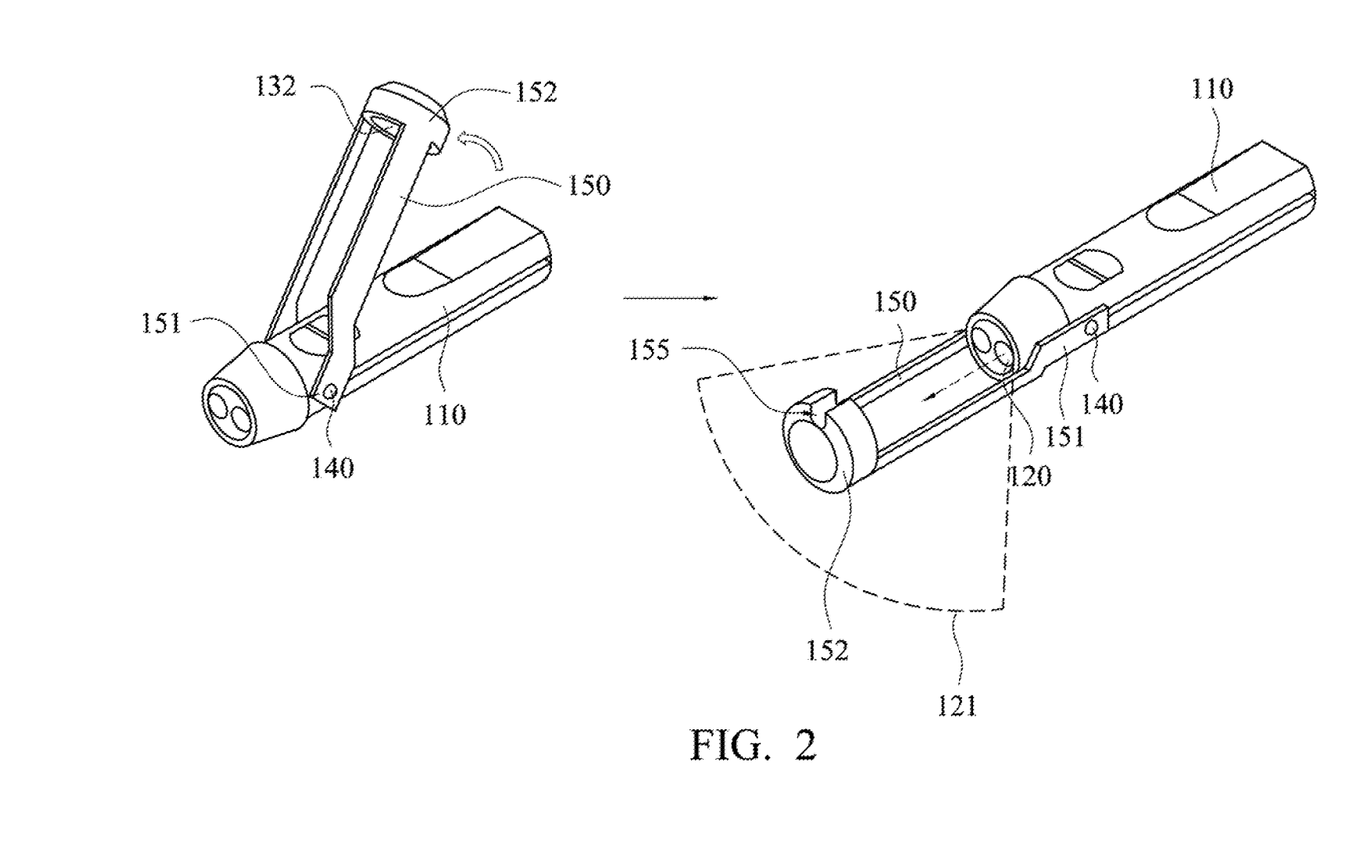
FIG. 2 is a diagram illustrating a top view of the optical sensing device transforming from a reflection mode into a penetration mode according to an embodiment.

The penetration mode is described below. Referring to FIG. 1 and FIG. 2, a light processing unit 132 is disposed on the transformation part 180 which is capable of pivoting so that light processing unit 132 may locate in the light working area 121. The light processing unit 132 is configured to emit or receive the light signal. For example, when the light processing unit 132 locates in the light working area 121, the light emitting unit 120 emits the light signal which would penetrate a biological tissue to generate a penetrating light signal, and the light processing unit 132 receives the penetrating light signal. Alternatively, the light signal may be emitted by the light processing unit 132, the penetrating light signal is generated after the light signal penetrates the biological tissue, and the penetrating light signal is received by the light receiving unit 131. As a result, the penetration measurement is done. In some embodiments, the transformation part 180 includes a connector 140 and an extending part 150. The connector 140 is disposed on the body 110. The extending part 150 has a first end 151 connected to the connector 140, and a second end 152. The extending part 150 rotates around the connector 140 so that the light processing unit 132 can locate in the light working area 121. In the penetration mode, the light signal emitted by the light emitting unit 120 or the light processing unit 132 is used to irradiate the biological tissue (e.g. finger) which is relatively thin.

In the embodiment, the light signal is configured to measure a physiological signal which may be blood oxygen concentration. In detail, the light emitting unit 120 or the light processing unit 132 may include a first optical emitting unit and a second optical emitting unit that are, for example, light emitting diodes, but the invention is not limited thereto. The first optical emitting unit and the second optical emitting unit respectively emit red light and infrared light. For example, the wavelength of the fight emitted by the optical emitting unit is ranged between 650 nanometer (nm) to 660 nm and the wavelength of the light emitted by the second optical emitting unit is ranged between 930 nm to 940 nm. Oxy-hemoglobin and deoxy-hemoglobin in the blood have different absorption rates to the light with the two wavelengths. Therefore, the blood oxygen concentration could be calculated according to the intensity of the light signal reflected by the biological tissue or the intensity of the light signal penetrating the biological tissue. However, the invention is not limited to the measurement of the blood oxygen concentration. Person in the art should be able to understand different biological tissue may have different absorption rates for different wavelengths of light. For example, blood has relatively high absorption rate for wavelength 520 nm to 532 nm, blood vessel has relatively high absorption rate for wavelength 1064 nm, and fat has relatively high absorption rate for wavelength 1720 nm. Therefore other physiological signals may be measured by using different wavelengths of light emitted by the optical emitting unit.

Figure 3:
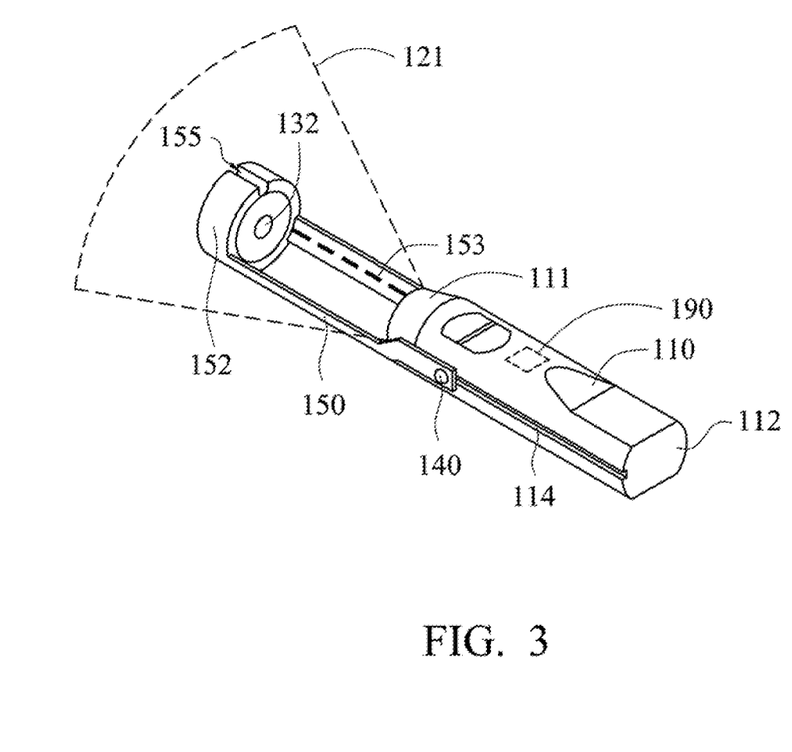
FIG. 3 is a diagram illustrating a top view of the optical sensing device in the penetration mode according to an embodiment.
Figure 4:
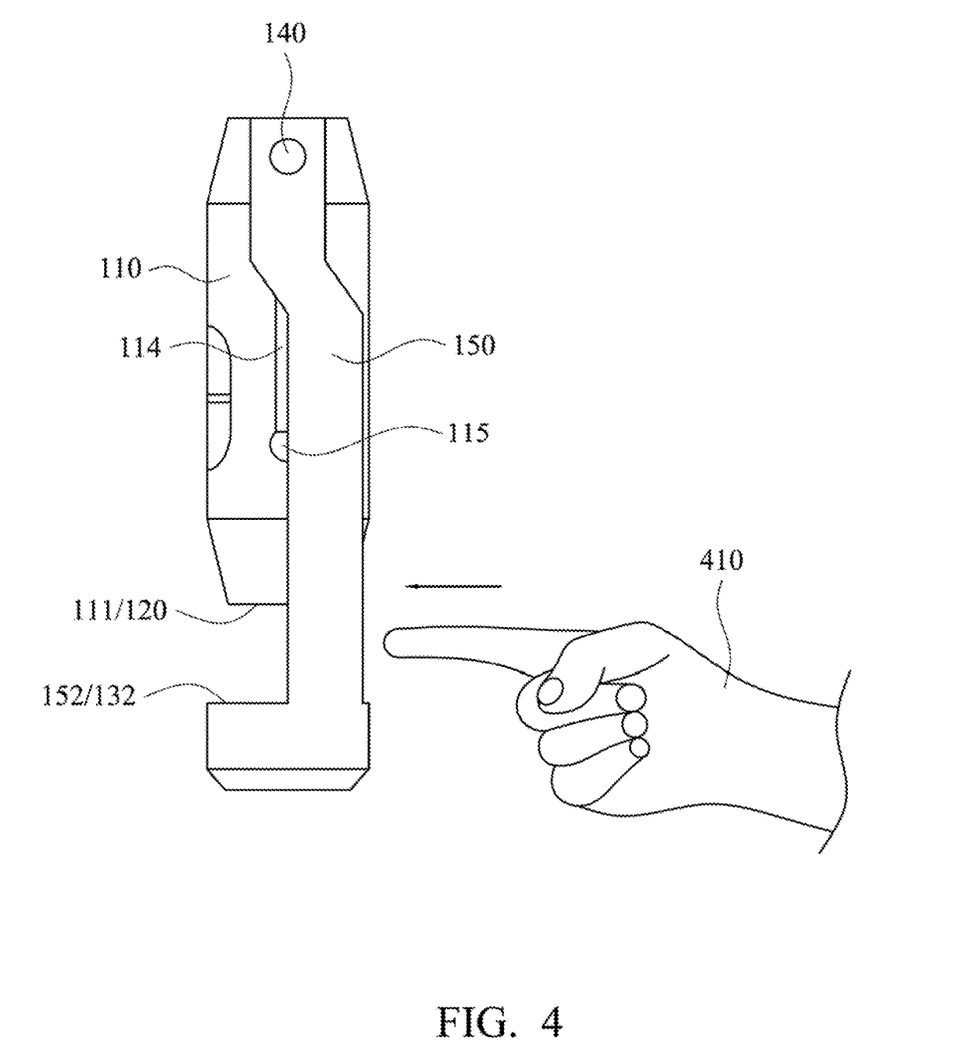
FIG. 4 is a schematic diagram illustrating the optical sensing device while sensing the finger in the penetration mode according to an embodiment.

In addition, referring to FIG. 3, the body 110 further has a track 114 disposed between the first end 111 and the second end 112 of the body 110, and the track 114 extends from the second end 112 to the first end 111. The connector 140 is disposed in the track 114. In the penetration mode, the connector 140 may move along the track 114 so as to change the distance between the second end 152 of the extending part 150 and the first end 111 of the body 110. On the other hand, a transmission line 153 is disposed in the extending part 150. The transmission line 153 has a first end electrically connected to the light processing unit 132, and a second end electrically connected to the signal unit 190. When the light processing unit 132 is configured to receive the penetrating light signal, the light processing unit 132 may transmit the measured electrical signal to the signal unit 190 through the transmission line 153. Alternatively, when the light processing unit 132 is configured to emit the light signal, the signal unit 190 may transmit a control signal to the light processing unit 132 through the transmission line 153 to emit the light signal. Referring to FIG. 4, a user may put his/her finger into a position between the first end 111 of the body 110 and the second end 152 of the extending part 150. The distance between the second end 152 of the extending part 150 and the first end 111 of the body 110 is changeable so that the second end 152 of the extending part 150 is close to the finger 410 to get better measurement effect. On the other hand, the body 110 has an indentation 115 disposed at one end of the track 114. When the connector 140 moves into the indentation 115, it would be fixed in the indentation 115.

In some embodiments, when the light processing unit 132 is configured to receive the penetrating light signal and locates in the light working area 121, the signal unit 190 turns off the light receiving unit 131 to avoid noises generated by the light receiving unit 131 in the penetration mode. In addition, when the light receiving unit 131 is configured to receive the reflected light signal and the light processing unit 132 does not locate in the light working area 121, the signal unit 190 turns off the light processing unit 132 to avoid noises generated by the light processing unit 132 in the reflection mode. In some embodiments, the signal unit 190 may measure the angle that the extending part 150 rotates in order to accordingly determine if the second end 152 of the extending part 150 locates in the light working area 121.

Figure 5:
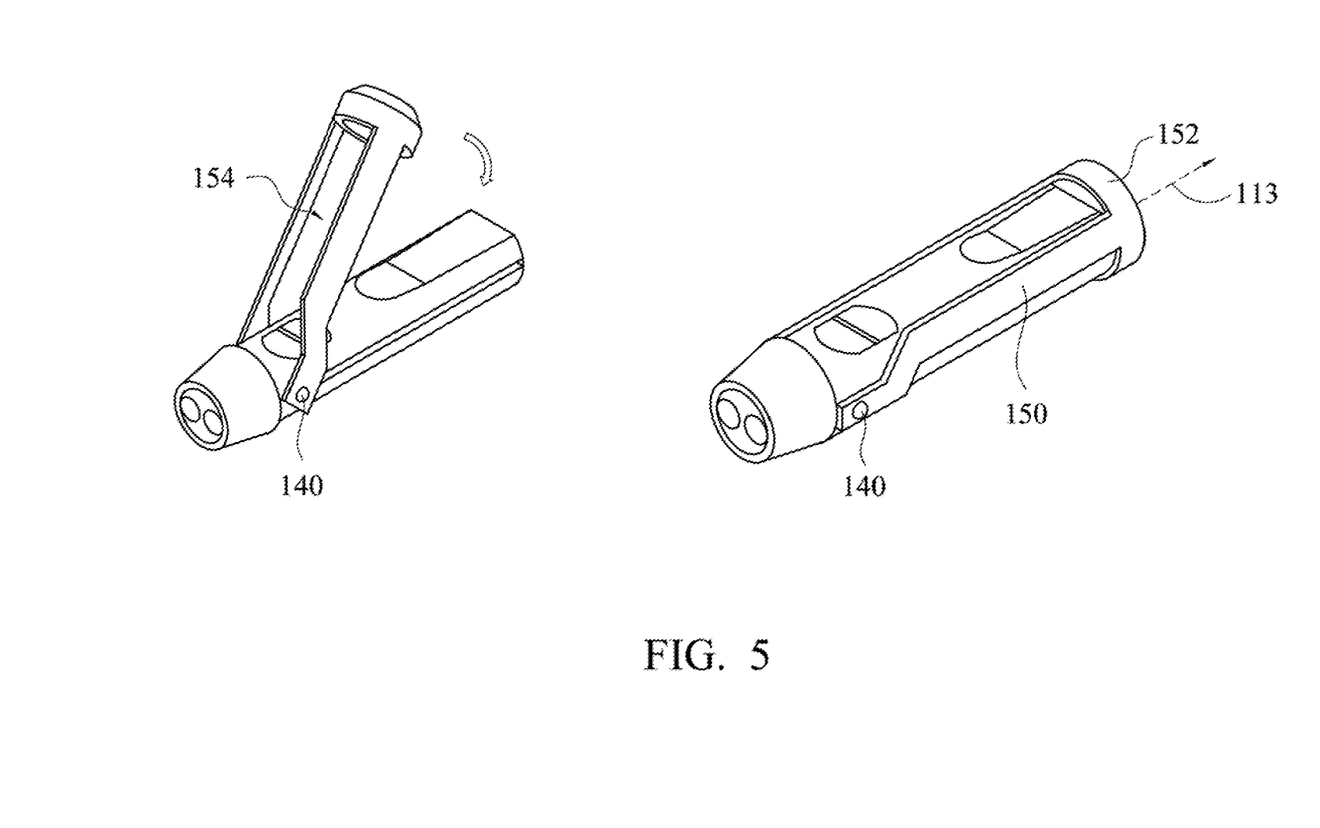
FIG. 5 is a diagram illustrating a top view of the optical sensing device transforming from the penetration mode to the reflection mode according to an embodiment.
Figure 6:
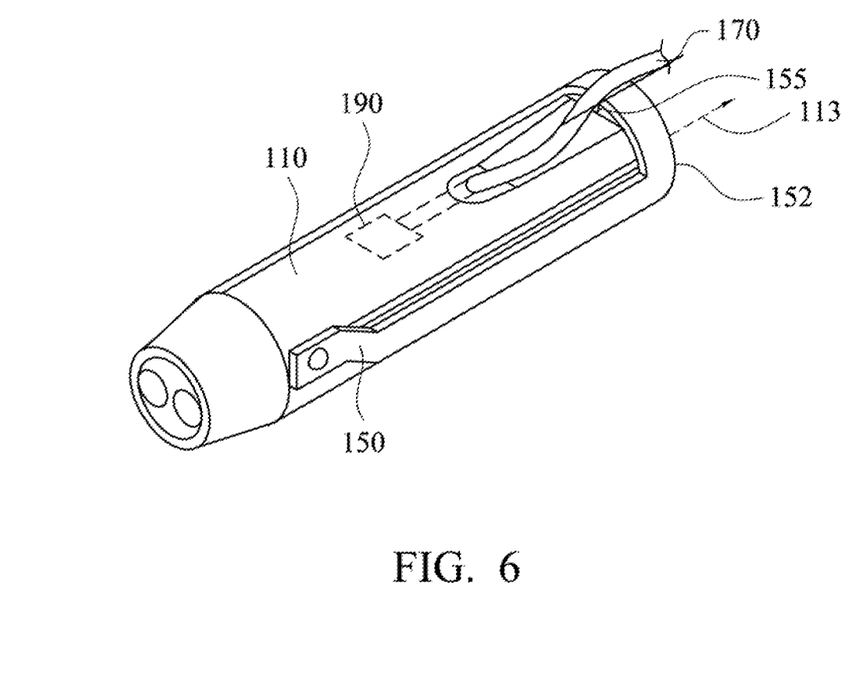
FIG. 6 is a top view of back side of the optical sensing device in the reflection mode according to an embodiment.

Referring to FIG. 5, the extending part 150 further has an opening 154, When the user switches the device from the penetration mode into the reflection mode, the extending part 150 rotates around the connector 140 and the body 110 passes through the opening 154 so that the second end 152 of the extending part 150 locates along an extending direction 113 from the second end 112 of the body 110. FIG. 6 is a top view of back side of the optical sensing device in the reflection mode according to an embodiment. Referring to FIG. 6, the optical sensing device 100 further includes a transmission line 170 having a first end electrically connected to the signal unit 190, and a second end electrically connected to another electrical device (not shown) for transmitting the detected electrical signal in the reflection mode or in the penetration mode to an external electrical device. Referring to FIG. 3 and FIG. 6, an indentation 155 is formed at the second end 152 of the extending part 150 to accommodate the transmission line 170. When the second end 152 of the extending part 150 locates along the extending direction 113, the transmission line 170 passes through the indentation 155.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fail within the

What is claimed is:

1. An optical sensing device for receiving and transmitting a light signal, wherein a light working area is defined according to a measurement range of the light signal, and the optical sensing device comprises:
   a body;
   a light emitting unit;
   a light receiving unit, wherein the light emitting unit and the light receiving unit are disposed at an end of the body, and the light emitting unit and the light receiving unit face the light working area;
   a transformation part configured to pivot on the body;
   a light processing unit disposed on the transformation part, wherein when the transformation part pivots so that the light processing unit locates in the light working area, the light processing unit is configured to transmit or receive the light signal; and
   a signal unit for transmitting and processing the light signal.

2. The optical sensing device of claim 1, wherein the transformation part comprises:
   a connector disposed on the body; and
   an extending part having a first end connected to the connector and a second end, wherein the light processing unit is disposed at the second end of the extending part, and the extending part is configured to rotate along the connector.

3. The optical sensing device of claim 2, wherein when the transformation part pivots so that the light processing unit locate in the light working area, the light emitting unit is configured to emit the light signal which penetrates a biological tissue to generate a penetrating light signal, and the light processing unit is configured to receive the penetrating light signal.

4. The optical sensing device of claim 3, wherein the signal unit is configured to turn off the light receiving unit.

5. The optical sensing device of claim 2, wherein when the transformation part pivots so that the light processing unit does not locate in the light working area, the light emitting unit is configured to transmit the light signal, and the light receiving unit is configured to receive a reflected light signal corresponding to the light signal.

6. The optical sensing device of claim 5, wherein the signal unit is configured to turn off the light processing unit.

7. The optical sensing device of claim 2, wherein a track is formed on the body, the track extends from a second end of the body to a first end of the body, and the connector is disposed in the track.

8. The optical sensing device of claim 2, wherein the extending part has an opening for the body to pass through.

9. The optical sensing device of claim 2, further comprising a first transmission line, wherein a first end of the first transmission line is electrically connected to the signal unit,
   wherein an indentation is formed at the second end of the extending part for accommodating the first transmission line.

10. The optical sensing device of claim 1, wherein a button is formed on the body for triggering the light emitting unit to emit the light signal.

* * * * *